(12) United States Patent
Khaw

(10) Patent No.: US 7,708,721 B2
(45) Date of Patent: May 4, 2010

(54) VASCULAR ACCESS NEEDLE

(75) Inventor: Kenneth Khaw, Plainsboro, NJ (US)

(73) Assignee: University of Medicine & Dentistry of New Jersey, Somerset, NJ (US)

(*) Notice: Subject to any disclaimer, the term of this patent is extended or adjusted under 35 U.S.C. 154(b) by 296 days.

(21) Appl. No.: 11/547,311

(22) PCT Filed: Apr. 5, 2005

(86) PCT No.: PCT/US2005/011818

§ 371 (c)(1),
(2), (4) Date: Jul. 12, 2007

(87) PCT Pub. No.: WO2005/096778

PCT Pub. Date: Oct. 20, 2005

(65) Prior Publication Data

US 2007/0276288 A1    Nov. 29, 2007

(51) Int. Cl.
*A61M 25/00* (2006.01)
(52) U.S. Cl. ...................................... 604/264
(58) Field of Classification Search .............. 604/159, 604/263, 187, 198, 197, 164.01, 164.08, 604/171, 162, 264; 606/213, 214
See application file for complete search history.

(56) References Cited

U.S. PATENT DOCUMENTS

| | | | | |
|---|---|---|---|---|
| 3,545,443 A | * | 12/1970 | Ansari | 604/160 |
| 4,022,191 A | | 5/1977 | Jamshidi | 128/2 |
| 4,798,193 A | | 1/1989 | Giesy et al. | 128/7 |
| 5,151,090 A | | 9/1992 | Best et al. | 604/192 |
| 5,219,332 A | * | 6/1993 | Nelson et al. | 604/528 |
| 5,322,515 A | | 6/1994 | Karas et al. | 604/192 |
| 5,380,290 A | | 1/1995 | Makower et al. | 604/164 |
| 6,398,743 B1 | | 6/2002 | Halseth et al. | 600/585 |

OTHER PUBLICATIONS

Braunwald: Heart Disease: A Textbook of Cardiovascular Medicine, 6th Ed., Copyright 2001, W.B. Saunders Company, p. 367.

* cited by examiner

*Primary Examiner*—Manuel A Mendez
(74) *Attorney, Agent, or Firm*—Klauber & Jackson, LLC

(57) ABSTRACT

A vascular access needle assembly is provided. The needle assembly includes a housing interconnected with a needle. The housing and the needle have slots along their lengths which are aligned to form a slot extending along the entire needle assembly. A sheath interconnected with the needle extends partially about the needle and includes a slot. The vascular access needle, with the needle point exposed and needle slot closed, can be inserted into the blood vessel of a subject and a guide wire can be inserted into the blood vessel through the needle assembly. The sheath is then moved to cover the needle point and to expose the needle slot so that the guide wire can be lifted through the needle, sheath and housing slots and the vascular access needle assembly removed, leaving the guide wire in the subject. The device can also be used as a wire introducer for catheters. The vascular needle assembly can also be used as a biopsy needle for obtaining biopsy tissue wherein the edges of one or both of the needle slot and sheath slot are sharpened for cutting tissue.

7 Claims, 16 Drawing Sheets

FIG. 2
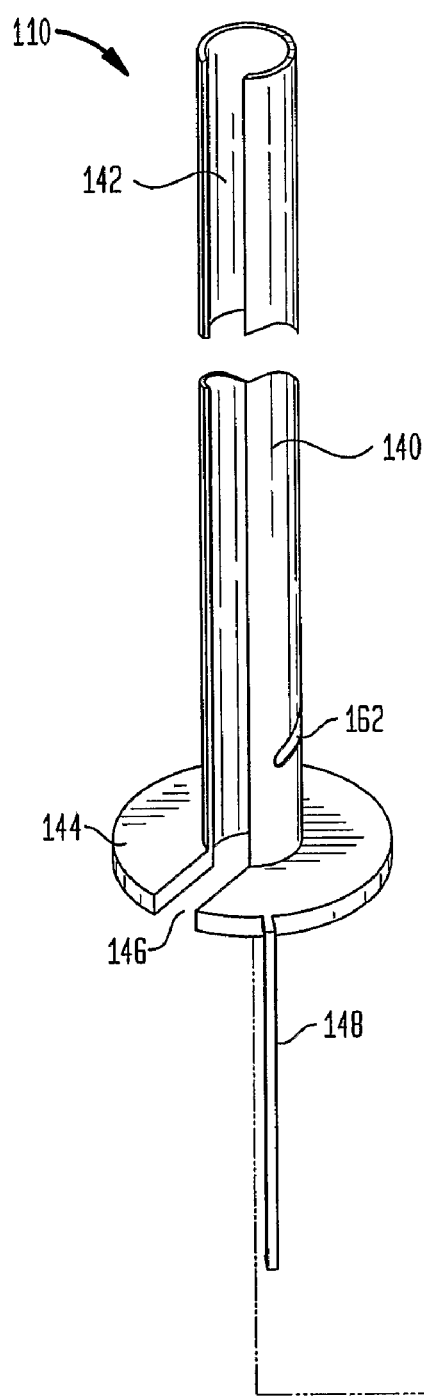
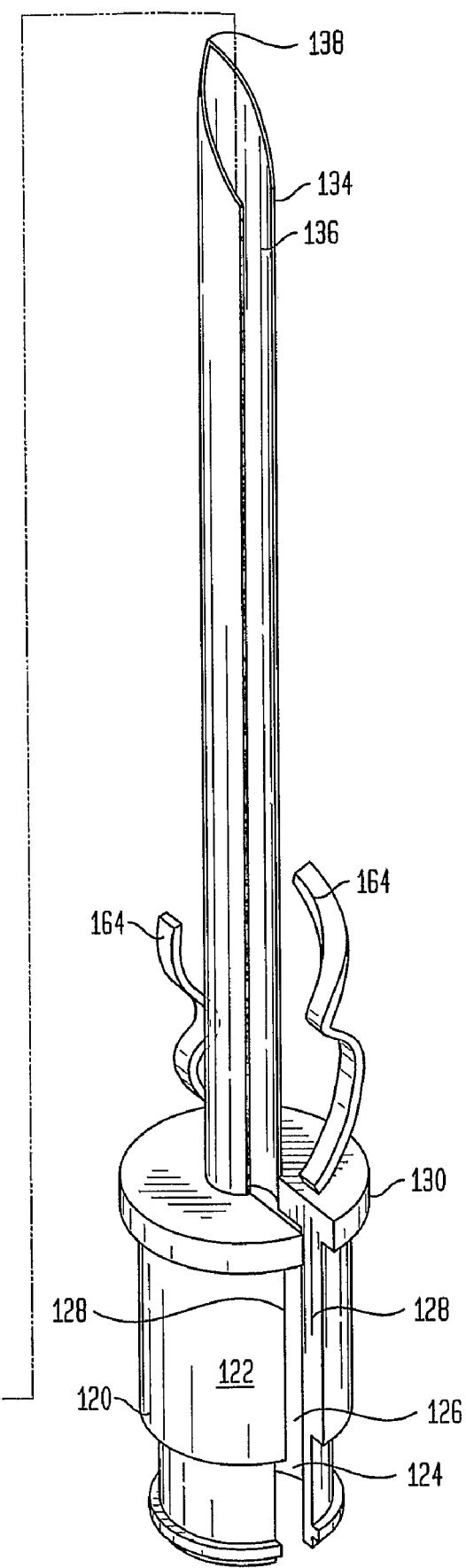

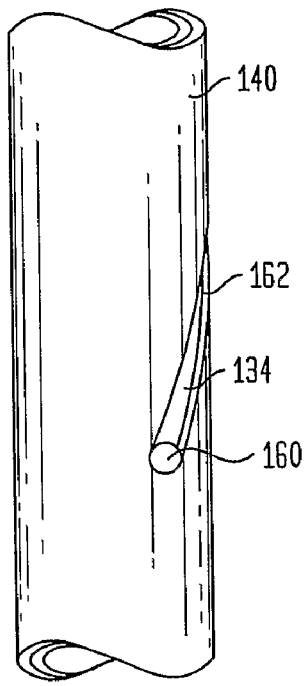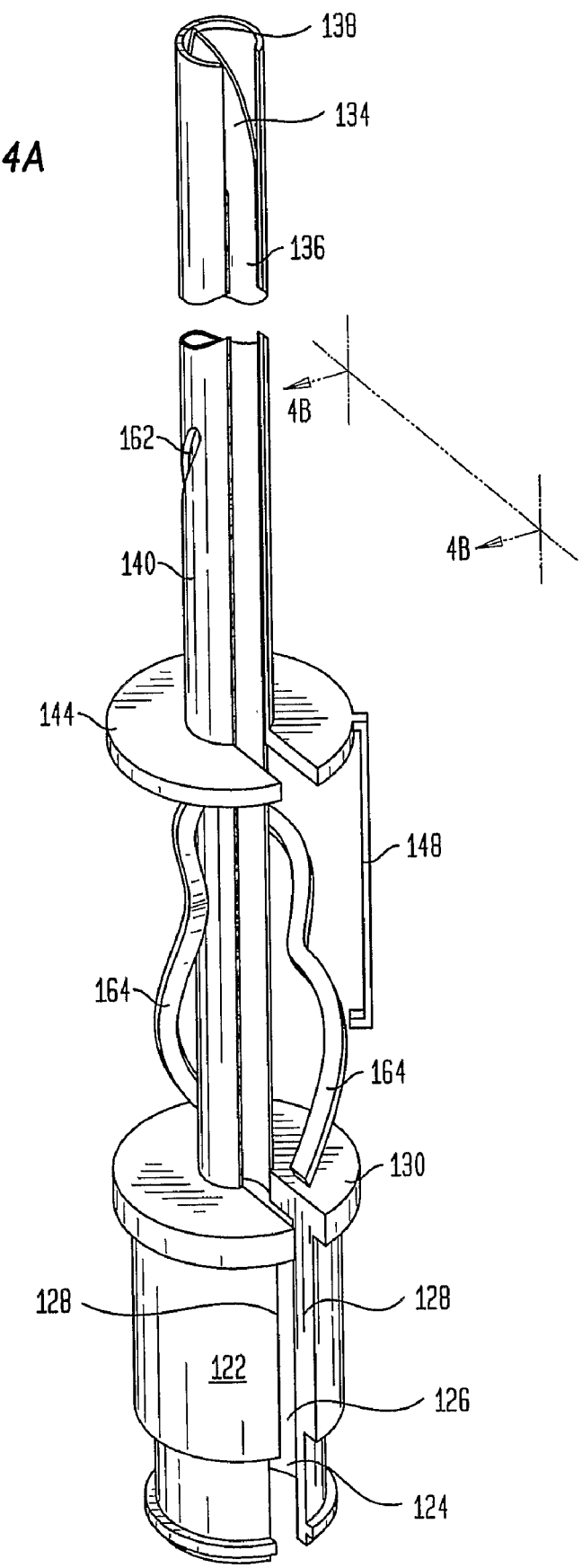

FIG. 10
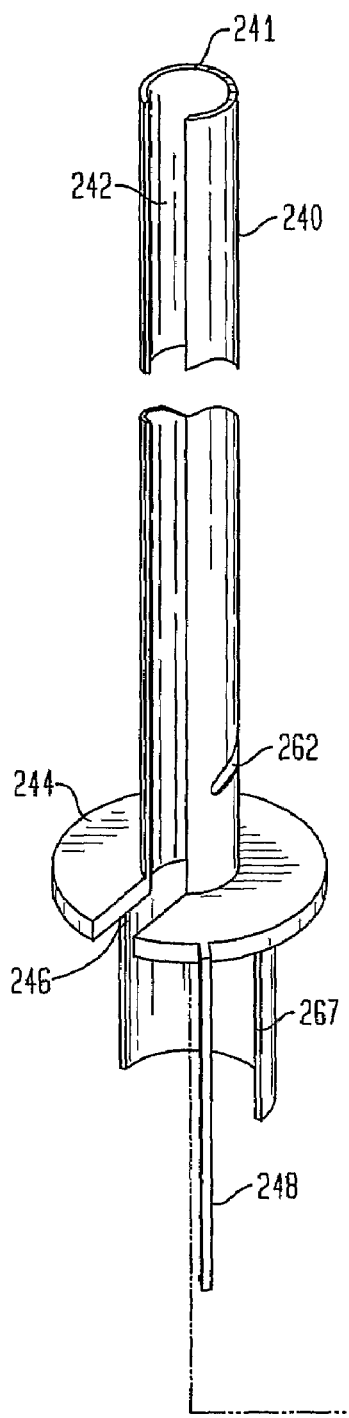
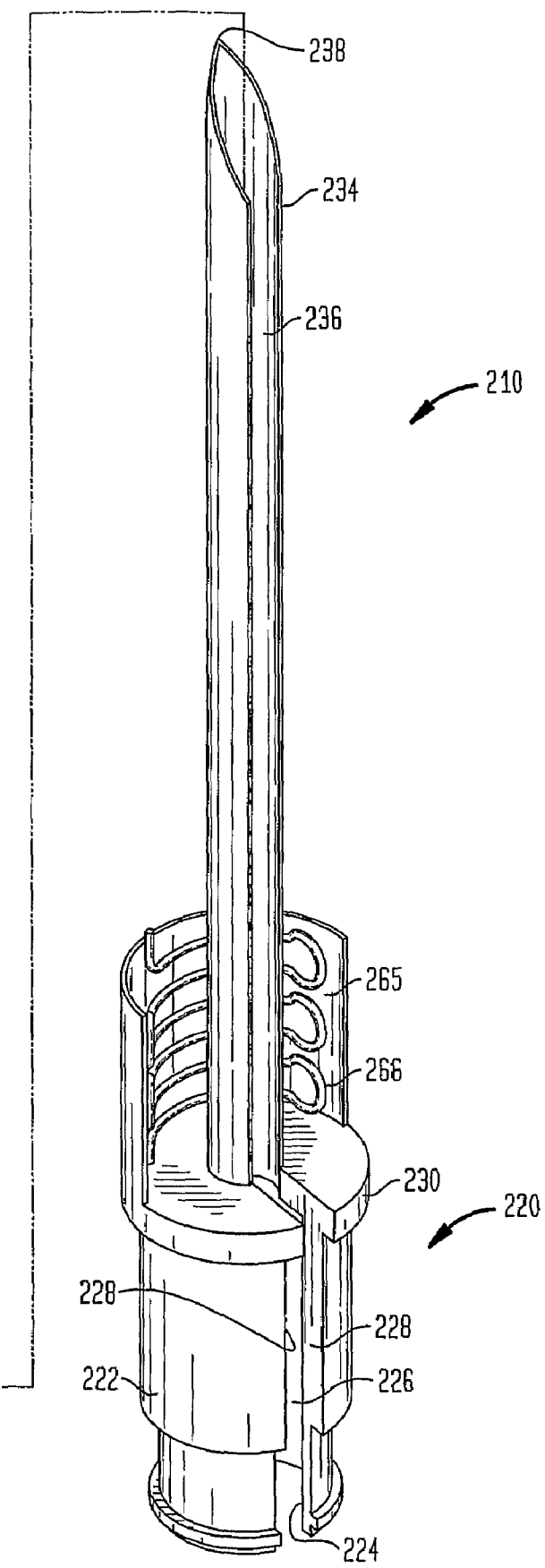

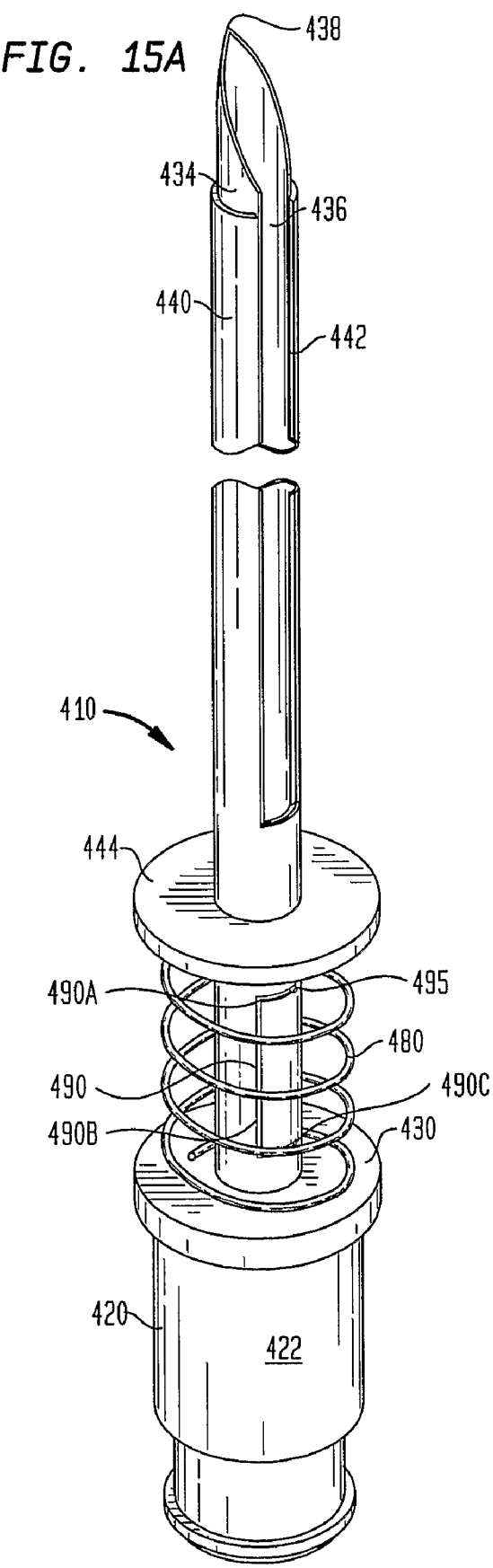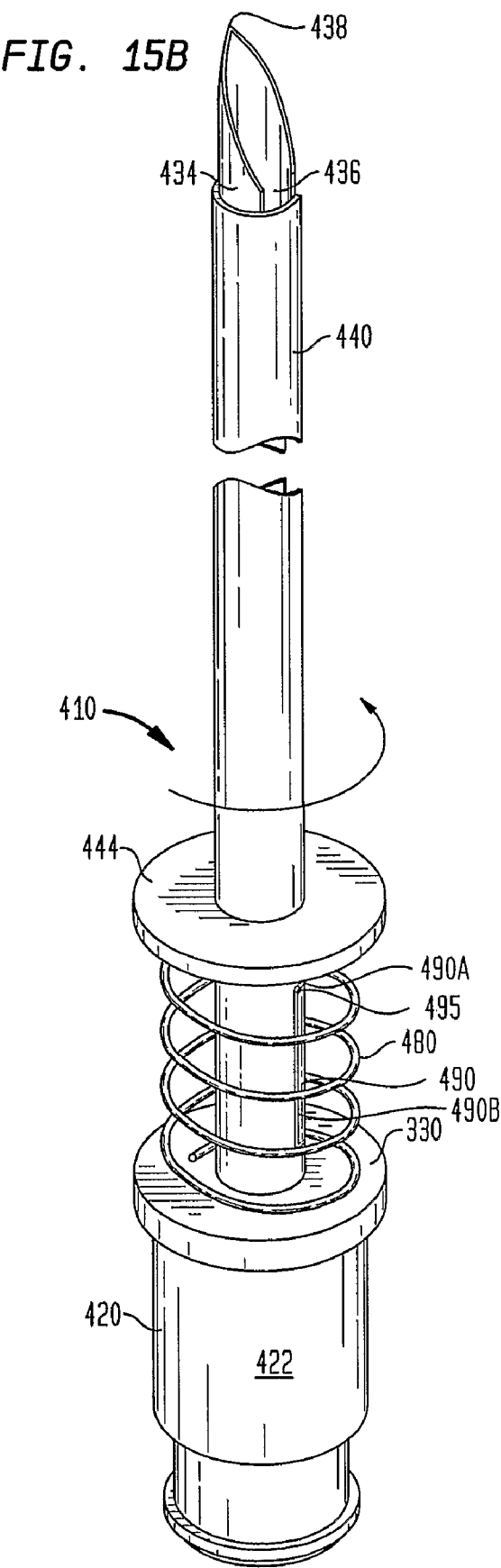

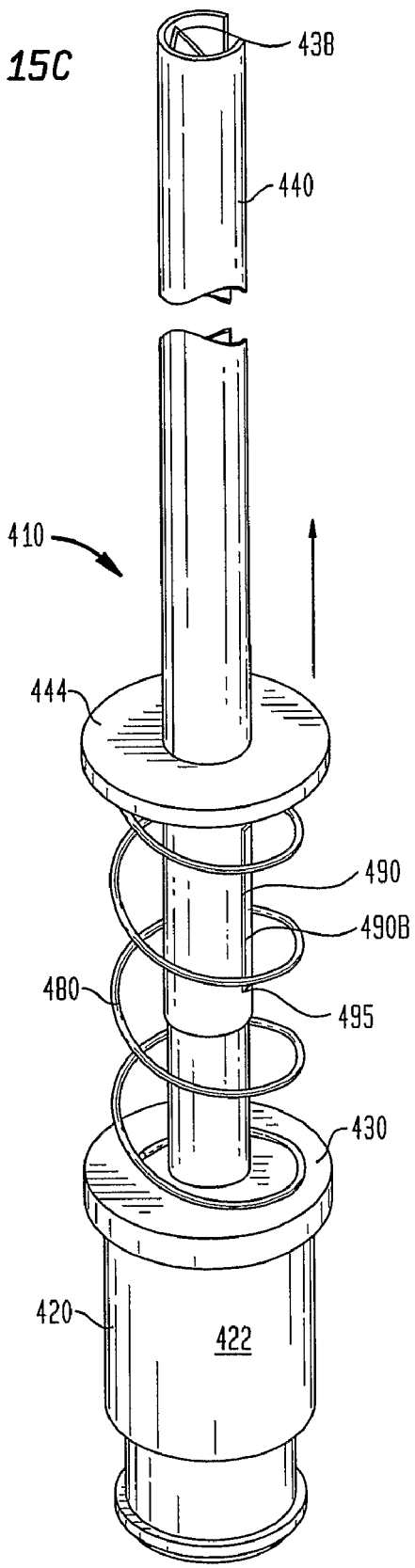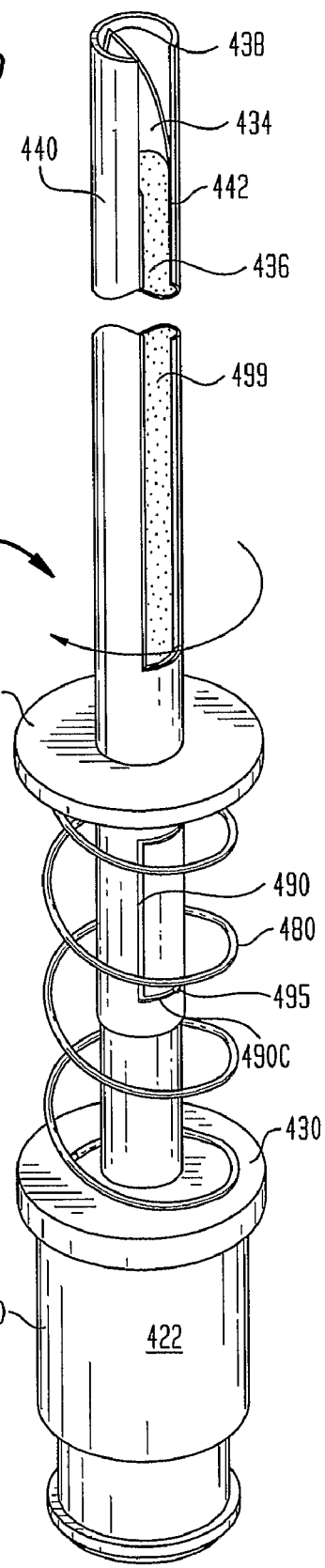

VASCULAR ACCESS NEEDLE

BACKGROUND OF THE INVENTION

1. Field of the Invention

The present invention relates to a medical device for inserting medical instruments into a subject. In particular, the invention provides a vascular access needle assembly to facilitate insertion of a guide wire into a subject.

2. Background of the Invention

Medical instruments used for diagnostic or therapeutic purposes such as micropuncture, catheterization, and arteriography are often introduced into subjects through vascular vessels using various types of needle assemblies. One problem associated with the use of such needles is inadvertent needle sticks.

The insertion of catheters and other instruments into blood vessels typically involves inserting and removing guide wires. For example, micropuncture involves inserting and removing guide wires of increasing diameter in order to successfully insert diagnostic or therapeutic instruments which may have a greater diameter than the initial insertion point into the blood vessel. One procedure involves making an incision in the skin over the target blood vessel. A thin walled needle is then inserted into the blood vessel. A fine guide wire is then inserted through the needle and the needle is removed by sliding it over the end of the guide wire. A dilator having inner and outer components is then placed over the guide wire, and is advanced over the guide wire and into the blood vessel. The inner component of the dilator and the guide wire are removed while the sheath (the outer component of the dilator) remains in the blood vessel. A guide wire of a larger diameter may then be inserted into the blood vessel. In addition to consuming valuable time, the disadvantage of this procedure is that in order to insert a device of greater diameter than the needle, more than one guide wire must be inserted and removed from the blood vessel, increasing the chances of damaging the vessel wall.

Other access and/or tissue collection procedures also have potential problems associated with the use of complicated devices and limitations much like those of vascular access needles.

Thus, what is needed, but has not yet been provided, is a vascular access needle which allows the insertion of instruments of varying or increasing diameter into a blood vessel without requiring the insertion of multiple guide wires, and which protects against inadvertent needle sticks. What is also needed is an access device which allows for quick and easy insertion of instruments. What is also needed is a device that allows for tissue to be quickly and easily obtained for biopsies.

SUMMARY OF THE INVENTION

A vascular access needle assembly is provided comprising a housing interconnected with a needle. The housing has a slot along its length and the needle has a slot along its length. The slots are aligned along the entire length of the needle assembly. The needle assembly additionally includes a sheath interconnected with the needle. The sheath extends partially about the needle and includes a slot. The sheath can be positioned such that its slot is aligned with the slot in the needle, or such that the sheath covers the slot in the needle. The sheath can be moved from a first position exposing the point of the needle for use, to a second position covering the point of the needle after use. A lock mechanism retains the sheath in a position exposing the needle point and covering the needle slot for use as a vascular access needle. A bias mechanism urges the sheath into a position covering the needle point and aligning the sheath and needle slots when the lock mechanism is released.

In use, the vascular access needle assembly is configured such that the sheath is locked in a first position to expose the needle point and cover the needle slot to form a vascular access needle assembly. The vascular access needle assembly is then inserted into a blood vessel of a subject as is known in the art. A guide wire is then inserted. The lock mechanism of the vascular access needle assembly is then released and the sheath moves to a second position covering the needle point and uncovering the needle slot. The guide wire can then be lifted through the needle and housing slot to remove the guide wire from the vascular access needle. The vascular access needle can then be removed from the subject and a dilator can be put into position in the subject over the guide wire. The vascular access needle, with the needle point covered by the sheath, can be discarded following known procedures.

The present invention can also be used to gain access into a small blood vessel for micropuncture procedures using a small needle. After insertion of the vascular access needle assembly into a blood vessel, a guide wire having a first reduced thickness can be inserted through the vascular access needle assembly of the invention and placed in the blood vessel. The sheath of the vascular access needle assembly can then be moved to cover the needle point and expose the needle slot. The guide wire can then be lifted out of the vascular access needle assembly through the slot and the vascular access needle assembly can be removed and discarded. The guide wire can then be further inserted into the blood vessel to position a second portion of the guide wire having a second increased thickness into the blood vessel.

The present invention can also be used as a wire introducer assembly to introduce wires into catheters in percutaneous procedures utilizing long thin wires. The wire introducer assembly comprises a housing interconnected with an inner cylindrical tube. The housing and the inner cylindrical tube have slots aligned along their lengths. An outer cylindrical tube slidably and rotatably interconnects with and extends partially about the inner cylindrical tube. The outer cylindrical tube includes a slot. The ends of the tubes of the wire introducer assembly can be blunt because there is no need for a sharp tip. The wire introducer assembly is inserted into a catheter which is inserted into a blood vessel. Initially, the outer cylindrical tube of the wire introducer assembly is positioned about the inner cylindrical tube to cover the slot in the inner cylindrical tube. A thin wire can be introduced into the wire introducer assembly through the inner cylindrical tube, and into the catheter. The outer cylindrical tube is then placed in a second position about the inner cylindrical tube to align the slots in the tubes. The long thin wire can then be lifted through the aligned slots. The wire introducer assembly can then be removed from the catheter without the need to slide the wire introducer assembly along the wire and off the end of the wire.

The vascular access needle assembly can also be used as a biopsy needle assembly to perform biopsies. In this embodiment, the edges of one or both of the needle slot and sheath slot of the biopsy needle assembly are sharpened for cutting body tissue. The biopsy needle assembly is configured such that the sheath and needle are placed in a first position to expose the needle point and to align the needle slot with the sheath slot. The biopsy needle assembly is then inserted into a tissue of a subject as is known in the art. A portion of tissue is forced into the needle core. The sheath and needle are moved with respect to each other to a second position wherein the sheath covers the needle slot. One or both of the edges of the sheath or needle are sharp such that their relative movement cuts the tissue. The tissue sample will be in the shape of a cylindrical core. To detach the tissue sample from the body of the patient, a syringe can be interconnected at the end of the biopsy needle assembly to aspirate or apply negative suction to loosen or tear the tissue at the needle tip. The sheath of the biopsy needle assembly can be moved to a third position to cover the needle point. The biopsy needle assembly can then be removed from the subject. Finally, the sheath can be moved to a fourth position exposing the slot in the needle so that the tissue sample can be withdrawn, while the needle point remains covered to prevent inadvertent needle sticks.

BRIEF DESCRIPTION OF THE DRAWINGS

Other important objects and features of the invention will be apparent from the following Detailed Description of the Invention taken in connection with the accompanying drawings in which:

FIG. 2 is an exploded perspective view of another embodiment of the vascular access needle assembly of the present invention.

FIG. 4A is a perspective view of the vascular access needle assembly shown in FIG. 3A with the sheath in a second position, the needle point covered, and the slots in the housing, needle, and sheath aligned. FIG. 4B is an enlarged view of guide pin is engaged with the guide slot in the sheath.

FIG. 10 is an exploded perspective view of another embodiment of the vascular access needle assembly of the present invention.

FIG. 15A is a perspective view of another embodiment of the vascular access needle assembly of the present invention as a biopsy needle assembly adapted for obtaining tissue samples for biopsies, with the sheath in a first position, exposing the needle point and needle slot. FIG. 15B is a perspective view of the biopsy needle assembly of the invention shown in FIG. 15A, with the sheath in a second position, covering the needle slot. FIG. 15C is a perspective view of the biopsy needle assembly shown in FIG. 15B, with the sheath in a third position, with the needle point covered. FIG. 15D is a perspective view of the biopsy needle assembly shown in FIG. 15C in a fourth position, with the needle point covered, and the needle slot and the tissue sample in the core of the needle exposed.

DETAILED DESCRIPTION OF THE INVENTION

The present invention relates to a vascular access needle assembly which includes a sheath movable from a first position to a second position for preventing inadvertent needle sticks after use. In the first position, the sheath covers a slot in the needle, and in a second position, the sheath exposes the slot to allow a guide wire to be lifted out through the slot. Accordingly, a guide wire having varying diameters can be inserted into a blood vessel.

Figure 1A:
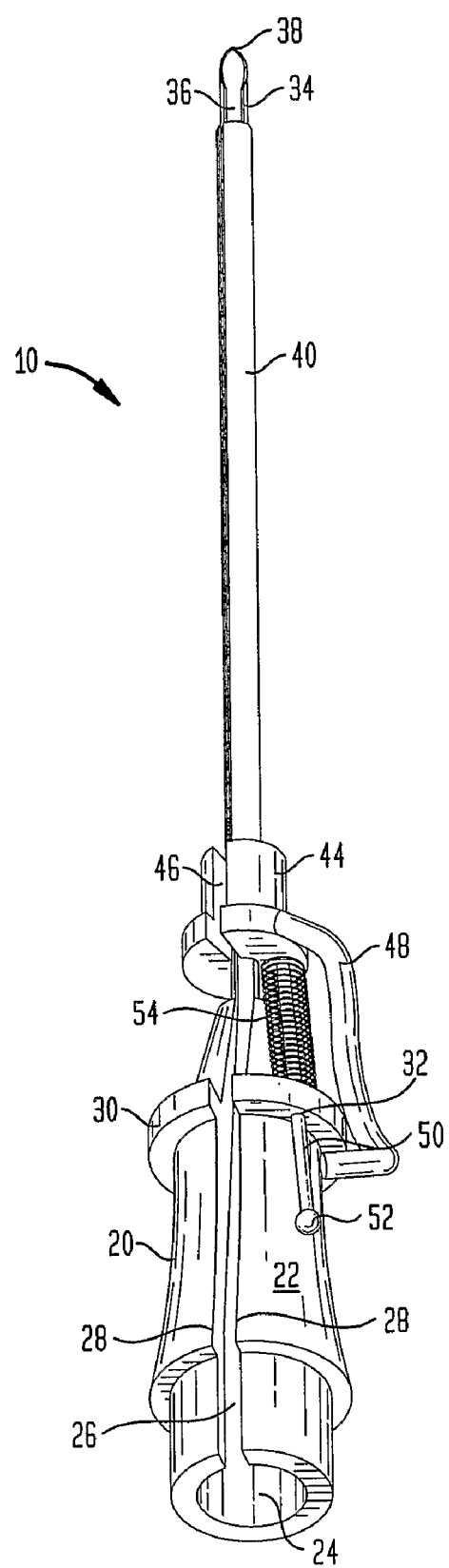
FIG. 1A is a perspective view of the vascular access needle assembly of the present invention with the sheath in a first locked position, exposing the needle point and covering the needle slot.
Figure 1B:
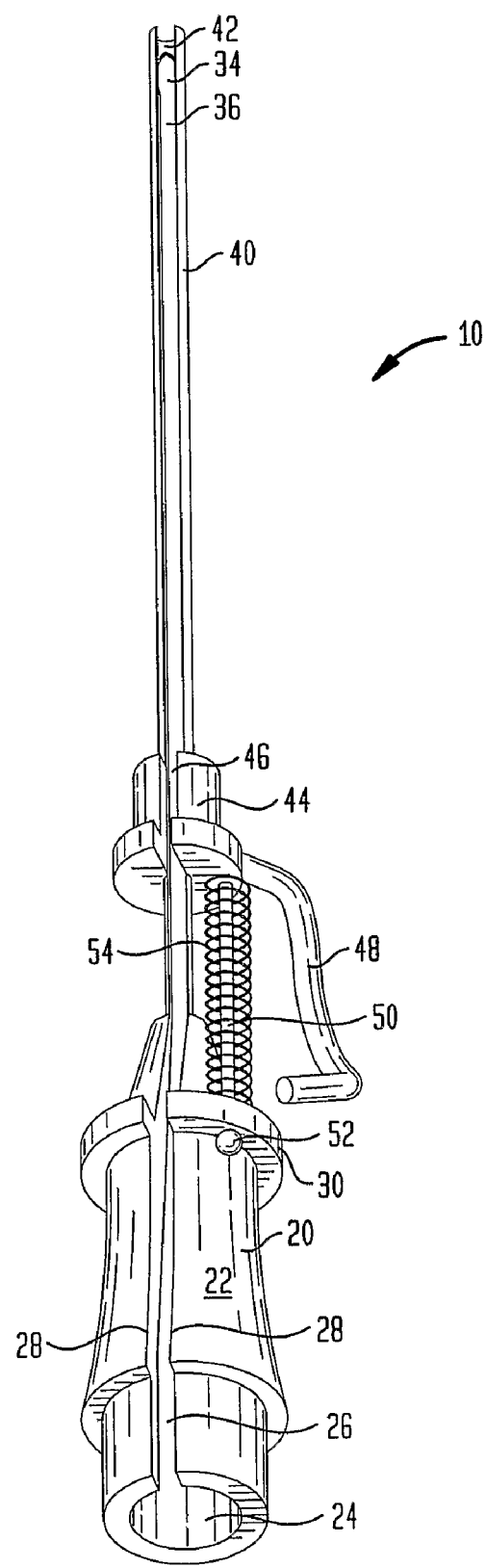
FIG. 1B is a perspective view of the vascular access needle assembly shown in FIG. 1A with the sheath in a second position, the needle point covered, and the slots in the housing, needle and sheath aligned.

As shown in FIGS. 1A and 1B, the vascular access needle assembly, generally indicated at 10, includes a housing 20 having an exterior surface 22 and an interior surface 24. Interior surface 24 is generally cylindrical and defines a lumen. Housing 20 can be made of plastic or other similar rigid material. Housing 20 has a slot 26 extending the length of housing 20 defined by walls 28 that extend from interior surface 24 to exterior surface 22 of housing 20.

A shoulder 30 can be provided on housing 20. As shown, shoulder 30 can be annular and extend around the circumference of exterior surface 22 of housing 20, shoulder 30 including a slot aligned with the slot in the housing. Alternatively, the shoulder can be confined to a tab or bracket on the housing. Shoulder 30 is configured to co-act with a sheath as will hereinafter be described.

A needle 34 is interconnected with and extends from housing 20. Needle 34 is generally cylindrical and has a point 38 at its distal end. Needle 34 includes a slot 36 extending along its length and which is aligned with slot 26 of housing 20.

A sheath 40 is slidably and rotationally engaged with needle 34. Sheath 40 covers substantially the length of needle 34. Sheath 40 has a slot 42 extending along its length. Sheath 40 can be interconnected at one end to a sheath housing 44 which is also positioned about needle 34. Sheath housing 44 includes a slot 46 aligned with slot 42 of sheath 40. Sheath 40 can be positioned in a first position with respect to needle 34 to cover needle slot 36 as shown in FIG. 1A. Sheath 40 can rotate and slide with respect to needle 34 to align sheath slot 42 with needle slot 36 and to cover needle point 38 as shown in FIG. 1B. At a minimum, sheath 40 has a width sized to cover slot 36 of needle 34. At a maximum, sheath 40 extends about needle 34, and needle slot 36 and sheath slot 42 are coextensive in width.

Sheath 40 and housing 20 are interconnected by a tether 50. As shown in FIG. 1, tether 50 could be a rod that is interconnected at one end to sheath housing 44 and at the other end with shoulder 30 of housing 20. Tether 50 extends through an aperture 32 in shoulder 30 and is held to shoulder 30 by a retainer 52 which is of sufficient size to be unable to pass through aperture 32. When sheath 40 covers needle slot 36, tether 50 is twisted such that the top of tether 50 is positioned nearly opposite of slot 36, i.e., the top of tether 50 is moved sufficiently to allow sheath 40 to cover needle slot 36. Tether 50 is thereby loaded such that when sheath 40 is unlocked, tether 50 rotates sheath 40 to uncover needle slot 36.

Vascular access needle assembly 10 further includes a locking mechanism which includes a locking arm 48 for holding sheath 40 in a first position on needle 34 such that slot 36 is covered and needle point 38 is exposed. Locking arm 48 can be attached at a first end to sheath 40 or, if present, to sheath housing 44. The second end of locking arm 48 releasably interconnects with housing 20, such as with shoulder 30 on housing 20, to retain sheath 40 in a first locked position. When sheath 40 is placed in the locked position, it rotates to cover needle slot 36, and thereby twisting tether 50.

Vascular access needle assembly 10 further includes a biasing mechanism. The biasing mechanism could include a spring 54 which is positioned about tether 50. Spring 54 urges sheath 40 to slide from a first position to a second position along needle 34. Tether 50 straightens to urge sheath 40 to rotate as it slides so that in the second position, sheath 40 covers needle point 38 and exposes needle slot 36.

FIG. 1A shows vascular access needle assembly 10 in a first locked position. Locking arm 48 is engaged at its second end to shoulder 30, compressing spring 54, twisting tether 50, and retaining sheath 40 in a position such that needle point 38 is exposed and sheath 40 covers needle slot 36. Tether 50 extends through aperture 32 of shoulder 30 with retainer 52 extending away from shoulder 30.

FIG. 1B shows vascular access needle assembly 10 in a second position. Locking arm 48 is released from engagement with shoulder 30, spring 54 slides sheath 40, and tether 50 straightens to rotate sheath 40 to a position where needle point 38 is covered by sheath 40 and needle slot 36 is exposed. Retainer 52 holds tether 50 in place and prevents sheath housing 46 and sheath 40 from sliding off over needle 34.

FIGS. 2-9 show another embodiment of the vascular access needle assembly of the present invention. FIG. 2 shows an exploded view of the vascular access needle assembly 110. Vascular access needle assembly 110 includes a housing 120 having an exterior surface 122 and an interior surface 124. Interior surface 124 is generally cylindrical and defines a lumen. Housing 120 has a slot 126, defined by walls 128, extending the length of housing 120. A shoulder 130 extends from exterior surface 122. Housing slot 126 extends through shoulder 130.

A needle 134 is interconnected with housing 120. Needle 134 has a point 138 and a slot 136 along its length. Needle slot 136 is aligned with housing slot 126. Springs 164 are interconnected with housing 120.

A sheath 140 has a slot 142 extending along its length. Sheath 140 can be interconnected at one end to a sheath housing 144. Sheath 140 slidably engages needle 134 and substantially covers the length thereof. Sheath housing 144 has a slot 146 which is aligned with sheath slot 142.

Figures 3A, 3B:
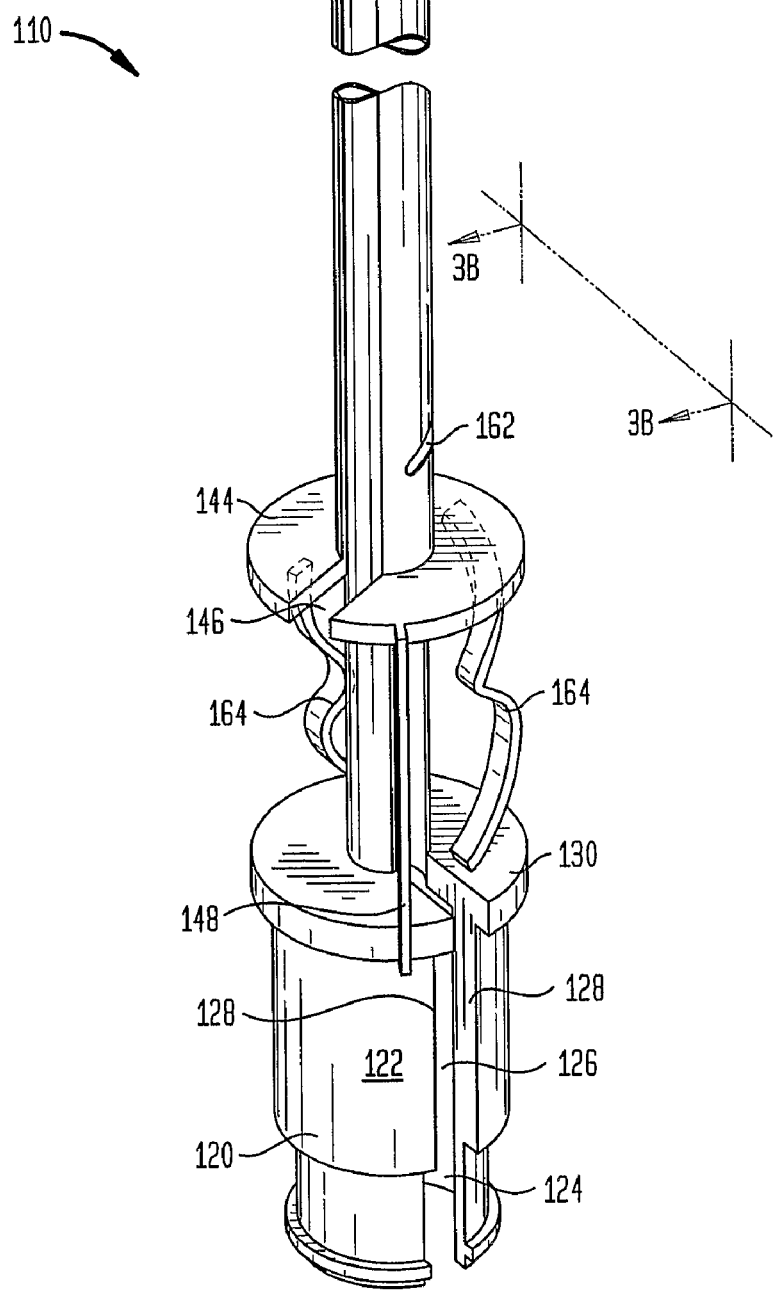
FIG. 3A is a perspective view of the vascular access needle assembly shown in FIG. 2 with the sheath in a first locked position, exposing the needle point and covering the needle slot.
FIG. 3B is an enlarged view of a guide pin on the needle engaged with a guide slot on the sheath.

A locking arm 148 extends from sheath 140 for retaining sheath 140 in a first position about needle 134 such that needle point 138 is exposed and needle slot 136 is covered. Locking arm 148 can be attached to sheath 140 or, as shown in FIG. 3A, to sheath housing 144. The second end of locking arm 148 is designed to be removably interconnected with shoulder 130 on housing 120 to retain sheath 140 in a locked position. As shown in FIG. 3A, locking arm 148 can be hooked to the edge of shoulder 130.

Vascular access needle assembly 110 further includes a rotational guide for orienting the sheath 140 and needle 134. As shown in FIG. 3B, sheath 140 includes a rotational guide slot 162 in the wall of sheath 140 which extends along a portion of sheath 140. A rotational guide pin 160 extends from needle 134 and is received in and is slidable along rotational guide slot 162.

Referring to FIG. 3A, vascular access needle assembly 110 is shown in a locked position. Locking arm 148 is engaged at its second end to shoulder 130. Springs, such as coiled or leaf springs 164, or any other suitable biasing mechanism, bear against sheath housing 144. As shown in FIG. 3B, rotational guide pin 160 is positioned at a first upper end of rotational guide slot 162. Needle point 138 is exposed and needle slot 136 is covered.

As shown in FIG. 4A, when locking arm 148 is released from engagement with shoulder 130, springs 164 slide sheath housing 144 along needle 134 such that sheath 140 covers needle point 138. At the same time, the rotational guide rotates sheath 140 about needle 134 so that needle slot 136 is exposed. As shown in FIG. 4B, rotational guide pin 160 is positioned at a second lower end of rotational guide slot 162.

Figure 5:
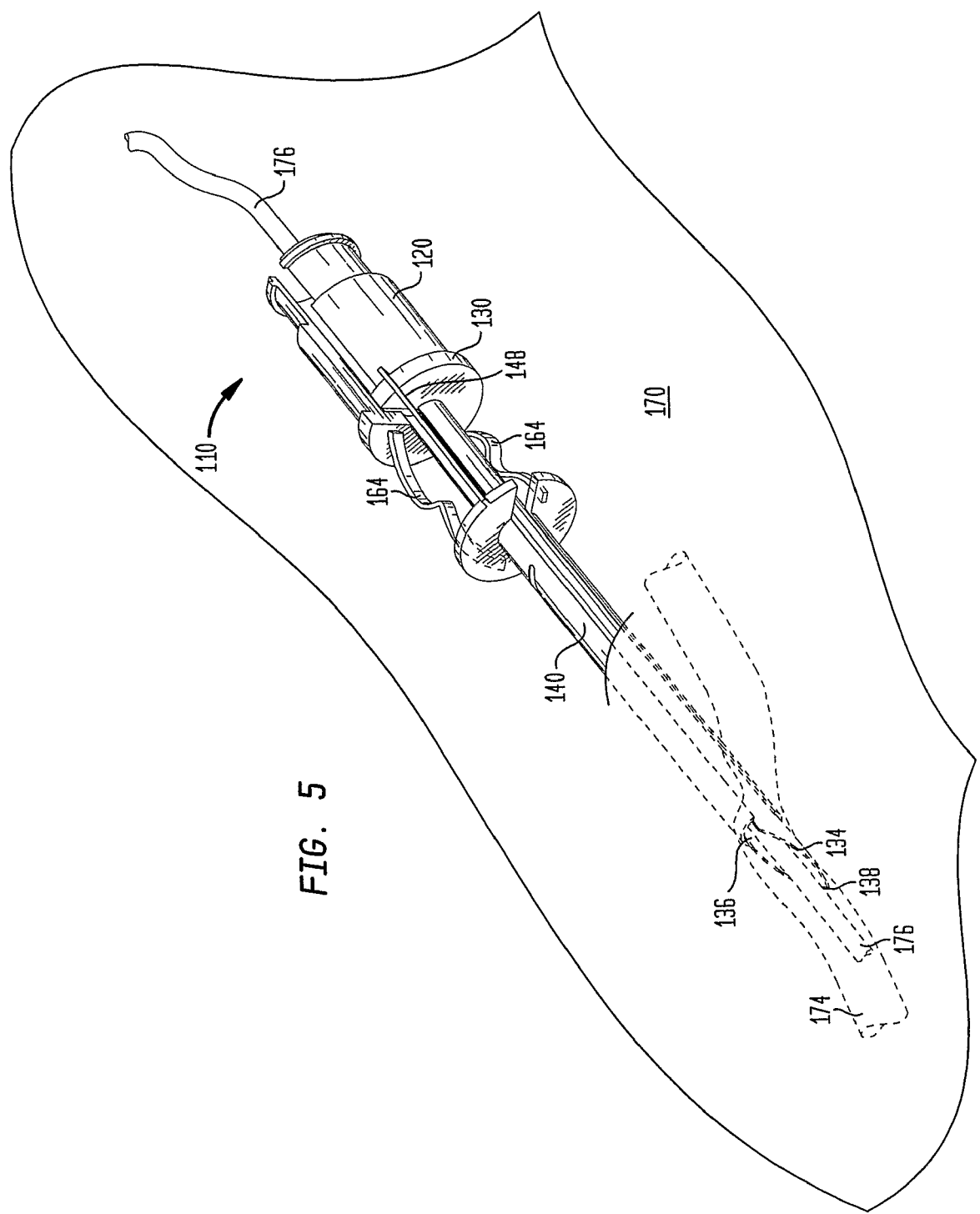
FIG. 5 shows the vascular access needle assembly of FIG. 3 inserted through the skin and into a blood vessel in a subject.

FIG. 5 shows vascular access needle assembly 110 inserted into a blood vessel 174 of a subject 170. Vascular access needle assembly 110 is in a first locked position, wherein locking arm 148 is engaged at its second end to shoulder 130, and springs 164 are compressed to hold sheath 140 in a position such that needle point 138 is exposed and needle slot 136 is covered, allowing needle 134 to pierce and access blood vessel 174. A guide wire 176 is inserted into the open end of housing 120 and up through needle 134 and into blood vessel 174.

Figure 6:
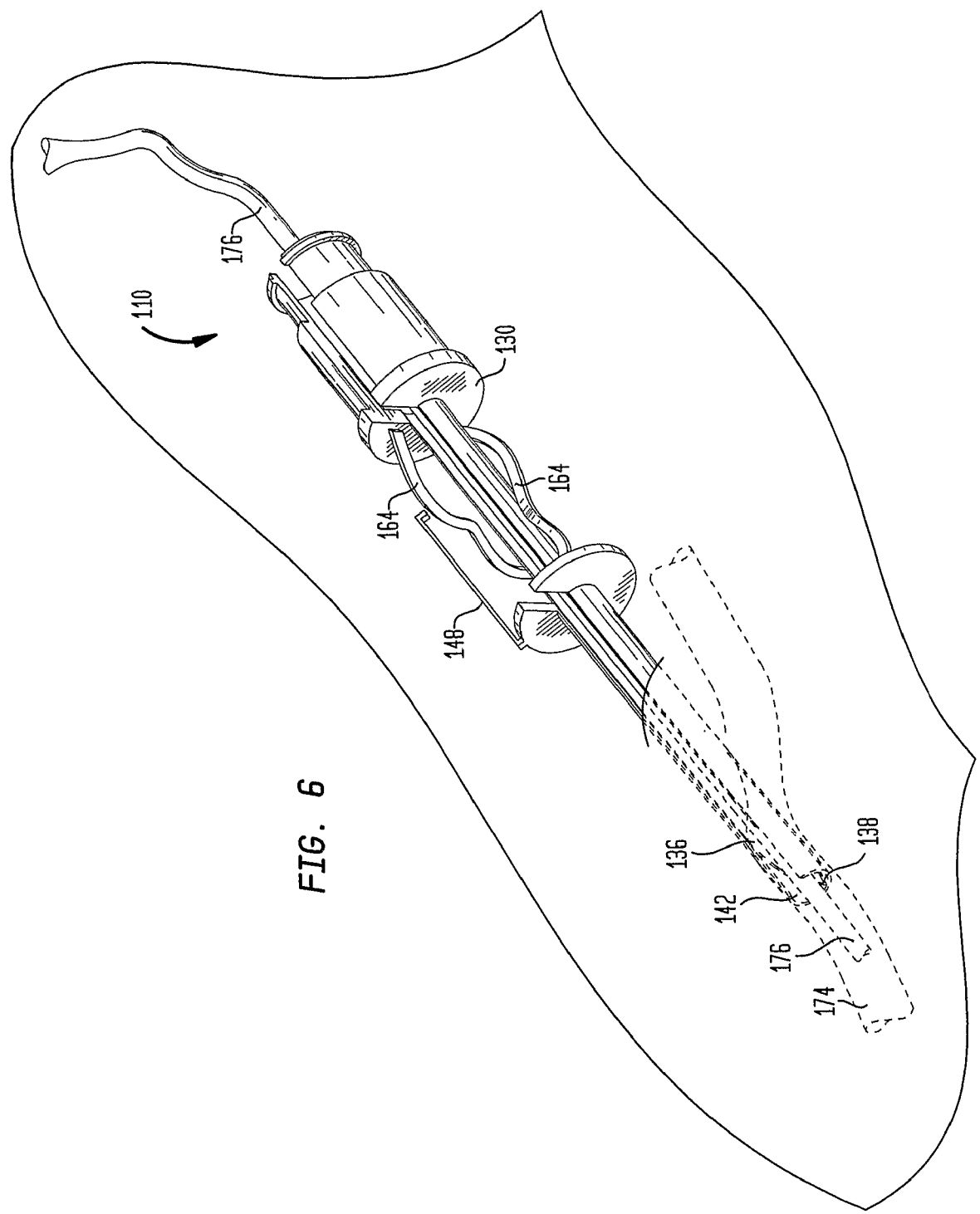
FIG. 6 shows the vascular access needle assembly shown in FIG. 5 with the sheath in a second position, covering the needle point and exposing the needle slot.
Figure 7:
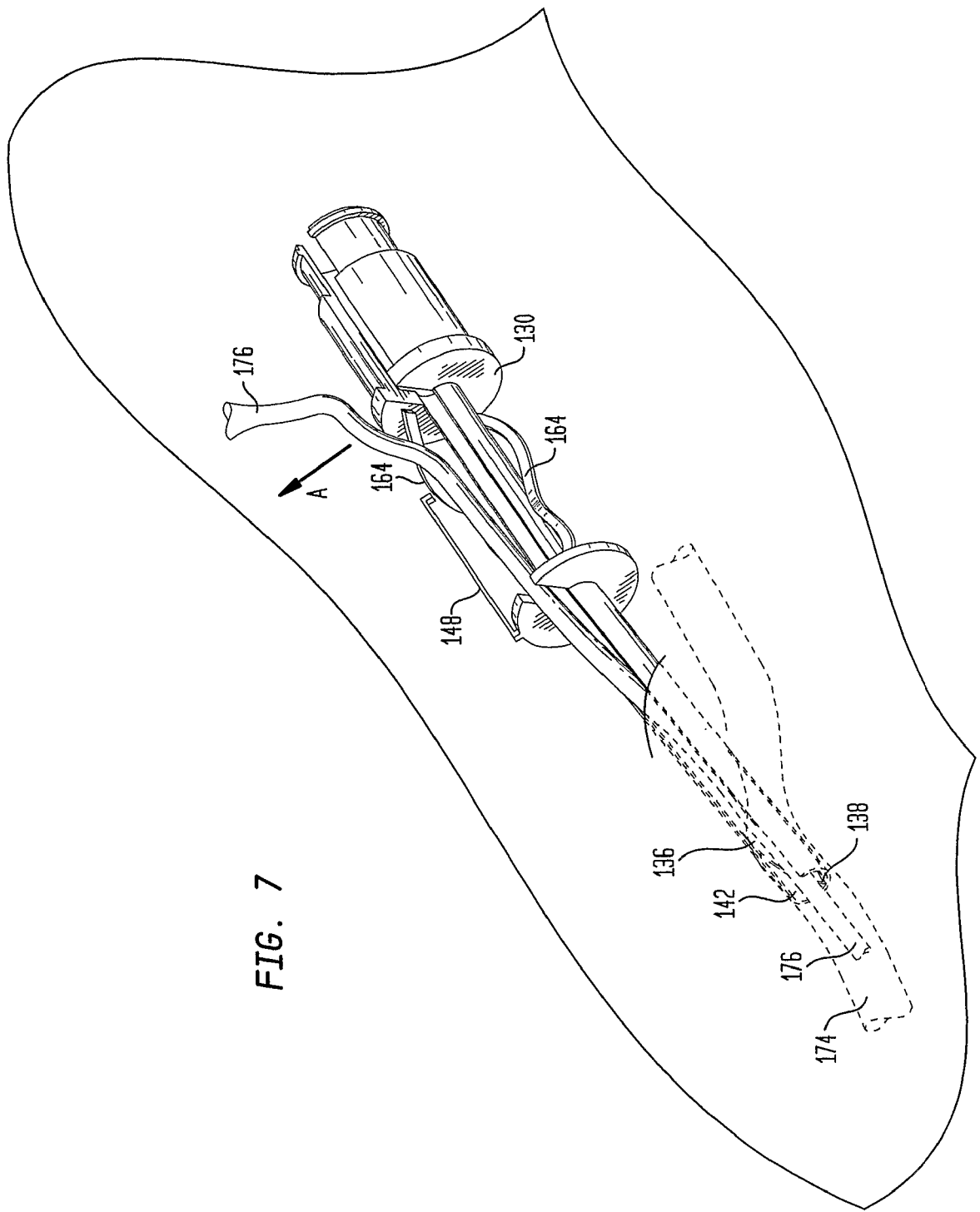
FIG. 7 shows the guide wire being lifted out of the slot of the vascular access needle assembly shown in FIG. 6.
Figure 8:
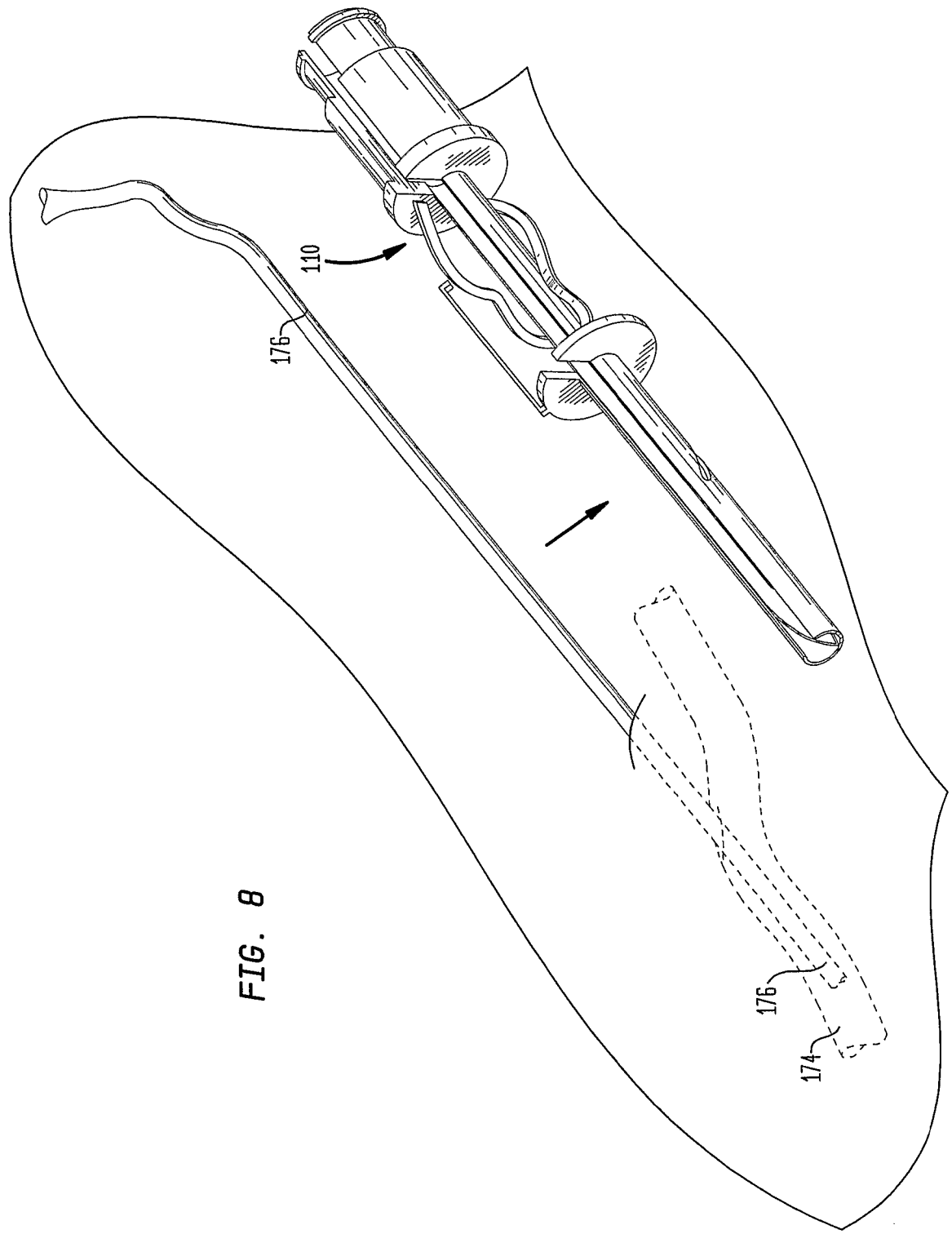
FIG. 8 shows the vascular access needle assembly removed from a subject with the guide wire left inserted into the blood vessel.

FIG. 6 shows vascular access needle assembly 110 inserted into blood vessel 174 wherein vascular access needle assembly 110 is in a second unlocked position. Locking arm 148 is released from engagement with shoulder 130, and springs 164 slide sheath 140 along needle 134 to cover needle point 138. The rotational guide rotates sheath 140 to align sheath slot 142 and needle slot 136 to expose needle slot 136. As shown in FIG. 7, guide wire 176 can then be lifted out of vascular access needle assembly 110 in the direction of Arrow A through needle slot 136 and sheath slot 142. As shown in FIG. 8, vascular access needle assembly 110 can then be removed from the insertion point, leaving guide wire 176 in blood vessel 174.

Figure 9:
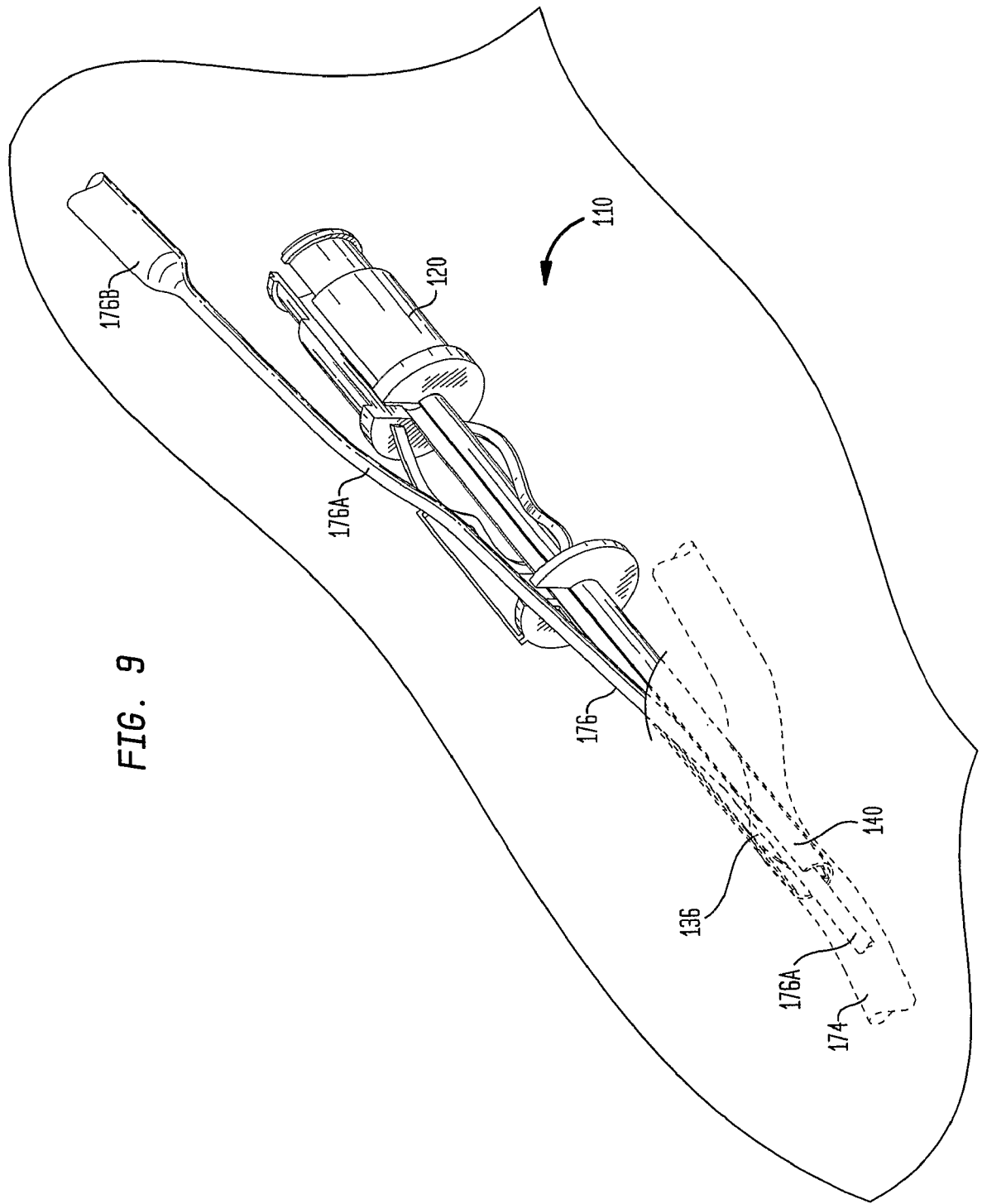
FIG. 9 shows the vascular access needle assembly of FIG. 3 with a guide wire having thick diameter portion and a thin diameter portion.

As shown in FIG. 9, vascular access needle assembly 110 may also be used for micropuncture procedures using an insertion wire 176 having a first portion 176A with a first diameter and a second portion 176B with a larger second diameter. The diameter of second portion 176B can be larger than the inner diameter of vascular access needle assembly 110. Thin portion 176A of guide wire 176 is inserted into the open end of housing 120 and into blood vessel 174. Thick portion 176B of guide wire 176 does not enter housing 120 of vascular access needle assembly 110.

After insertion of vascular access needle assembly 110, sheath 140 is moved to expose needle slot 136. Guide wire 176 is then lifted out of vascular access needle assembly 110 through needle slot 136 and vascular access needle assembly 110 is removed from the subject. Thick portion 176B of guide wire 176 can then be fed into blood vessel 174 and a dilator can then be inserted to perform the medical procedure. In this manner, the multiple steps of inserting a dilator having an inner and outer sheath over a thin guide wire, withdrawing the thin guide wire and inner sheath of the dilator, inserting a thicker guide wire through the outer sheath of the dilator, and removing the outer sheath of the dilator to perform the medical procedure are avoided.

FIG. 10 shows an exploded view of yet another embodiment of the vascular access needle assembly of the present invention. A vascular access needle assembly 210 includes a housing 220 having an exterior surface 222 and an interior surface 224. Interior surface 224 is generally cylindrical and defines a lumen. Housing 220 has a slot 226, defined by walls 228, extending the length of housing 220. A shoulder 230 extends from exterior surface 222. Housing slot 226 extends through shoulder 230.

A needle 234 is interconnected with housing 230. Needle 234 has a point 238 and a slot 236 along its length. Needle slot 236 is aligned with housing slot 226. A needle retaining wall 265 extends from shoulder 230 and partially about needle 234. A spring 266 is interconnected with housing 220 and is positioned adjacent an interior of retaining wall 265.

A sheath 240 has a slot 242 extending along its length. Sheath 240 can be interconnected at one end to a sheath housing 244. Sheath 240 slidably engages needle 234 and substantially covers the length thereof. Sheath housing 244 has a slot 246 which is aligned with sheath slot 242. A sheath retaining wall 267 extends from sheath housing 244 and partially about sheath 240. When sheath 240 is slidably engaged with needle 234, sheath retaining wall 267 is positioned between spring 266 and needle 234. Needle retaining wall 265 and sheath retaining wall 267 extend alongside each other and form a channel for maintaining spring 266 in position.

A locking arm 248 extends from sheath housing 244 for retaining sheath 240 in a first position about needle 234 such that needle point 238 is exposed and needle slot 236 is covered. The second end of locking arm 248 is designed to be removably interconnected with shoulder 230 on housing 220 to retain sheath 240 in the locked position.

Vascular access needle assembly 210 further includes a rotational guide for orienting sheath 240 and needle 234. Sheath 240 includes a rotational guide slot 262 in the wall of sheath 240 which extends along a portion of sheath 240. A rotational guide pin extending from needle 234 is received in and is slidable along rotational guide slot 262.

As can be readily appreciated, the embodiment of the invention shown in FIGS. 1A and 1B and the embodiment shown in FIG. 10 can be operated in the same manner described with respect to the embodiment shown in FIGS. 7-9.

Figure 11:
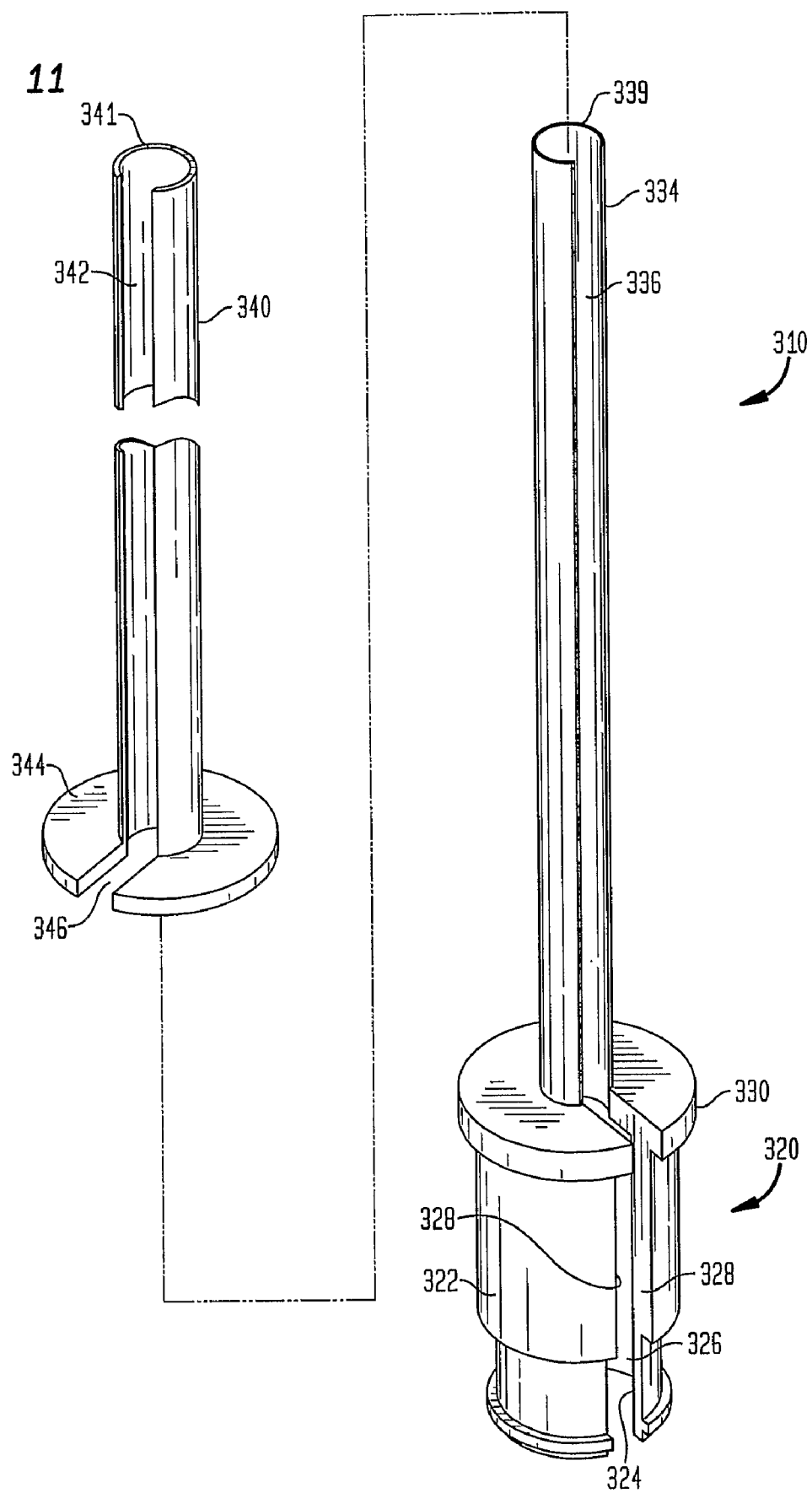
FIG. 11 is an exploded perspective view of another embodiment of the vascular access needle assembly of the present invention as a wire introducer assembly for insertion of instruments through a catheter.

FIGS. 11-14 show yet another embodiment of the present invention used as a wire introducer assembly for inserting instruments through a catheter. FIG. 11 shows an exploded view of a wire introducer assembly 310. The wire introducer assembly 310 includes a housing 320 having an exterior surface 322 and an interior surface 324. Interior surface 324 is generally cylindrical and defines a lumen. Housing 320 has a slot 326, defined by walls 328, extending the length of housing 320. A shoulder 330 extends from exterior surface 322. Housing slot 326 extends through shoulder 330.

An inner cylindrical tube 334 is interconnected with housing 320. Inner cylindrical tube 334 has a blunt end 339 and a slot 336 along its length. Inner tube slot 336 is aligned with housing slot 326.

An outer cylindrical tube 340 has a slot 342 extending along its length, and an end 341. Outer cylindrical tube 340 can be interconnected at one end to outer tube housing 344. Outer cylindrical tube 340 slidably engages inner cylindrical tube 334 and substantially covers the length thereof. Outer tube housing 344 has a slot 346 which is a continuation of slot 342 of outer cylindrical tube 340. When assembled, outer cylindrical tube 340 may be rotated or twisted to either expose or cover inner tube slot 336.

Figure 12:
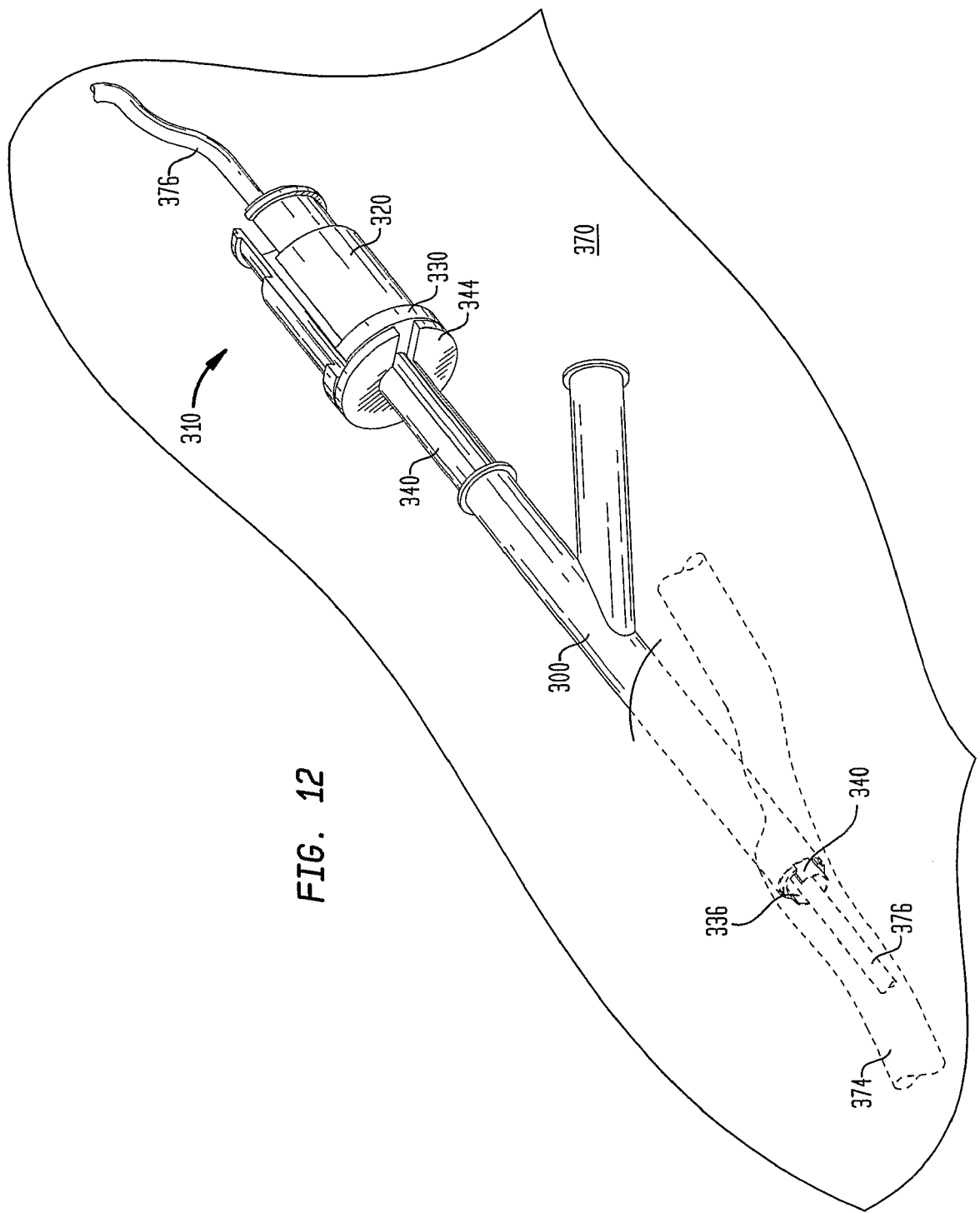
FIG. 12 shows the wire introducer assembly of FIG. 11 inserted into a catheter assembly with a guide wire inserted through the wire introducer needle assembly and catheter and into the body.

FIG. 12 shows wire introducer assembly 310 of FIG. 11 inserted into one opening of a catheter assembly 300 which is inserted into a blood vessel 374 of a subject 370. Wire introducer assembly 310 is in a first position, wherein outer cylindrical tube 340 covers inner tube slot 336. A guide wire 376 is inserted into the open end of housing 320 and into blood vessel 374.

Figure 13:
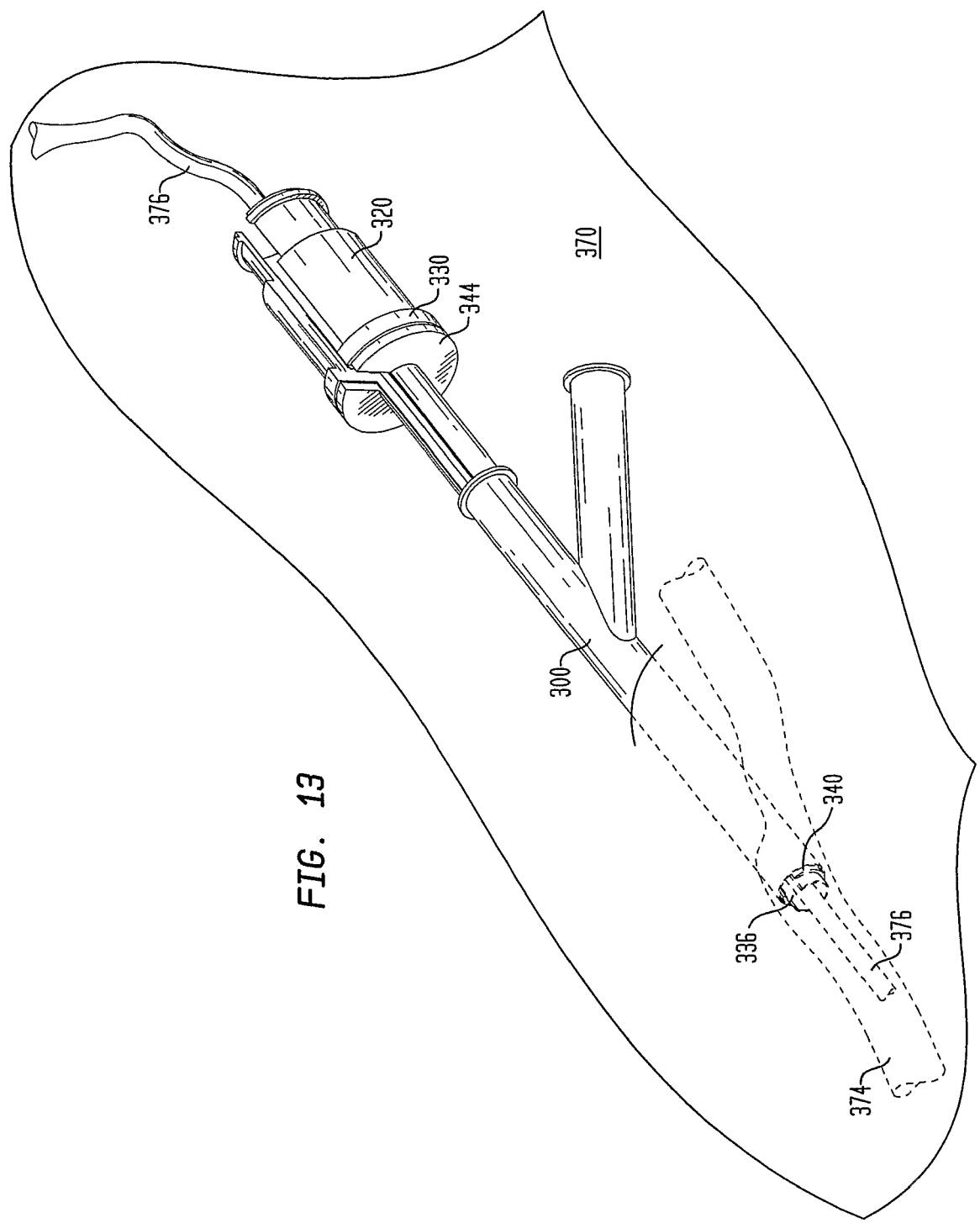
FIG. 13 shows the wire introducer assembly shown in FIG. 12 with the sheath in a second position exposing the needle slot.
Figure 14:
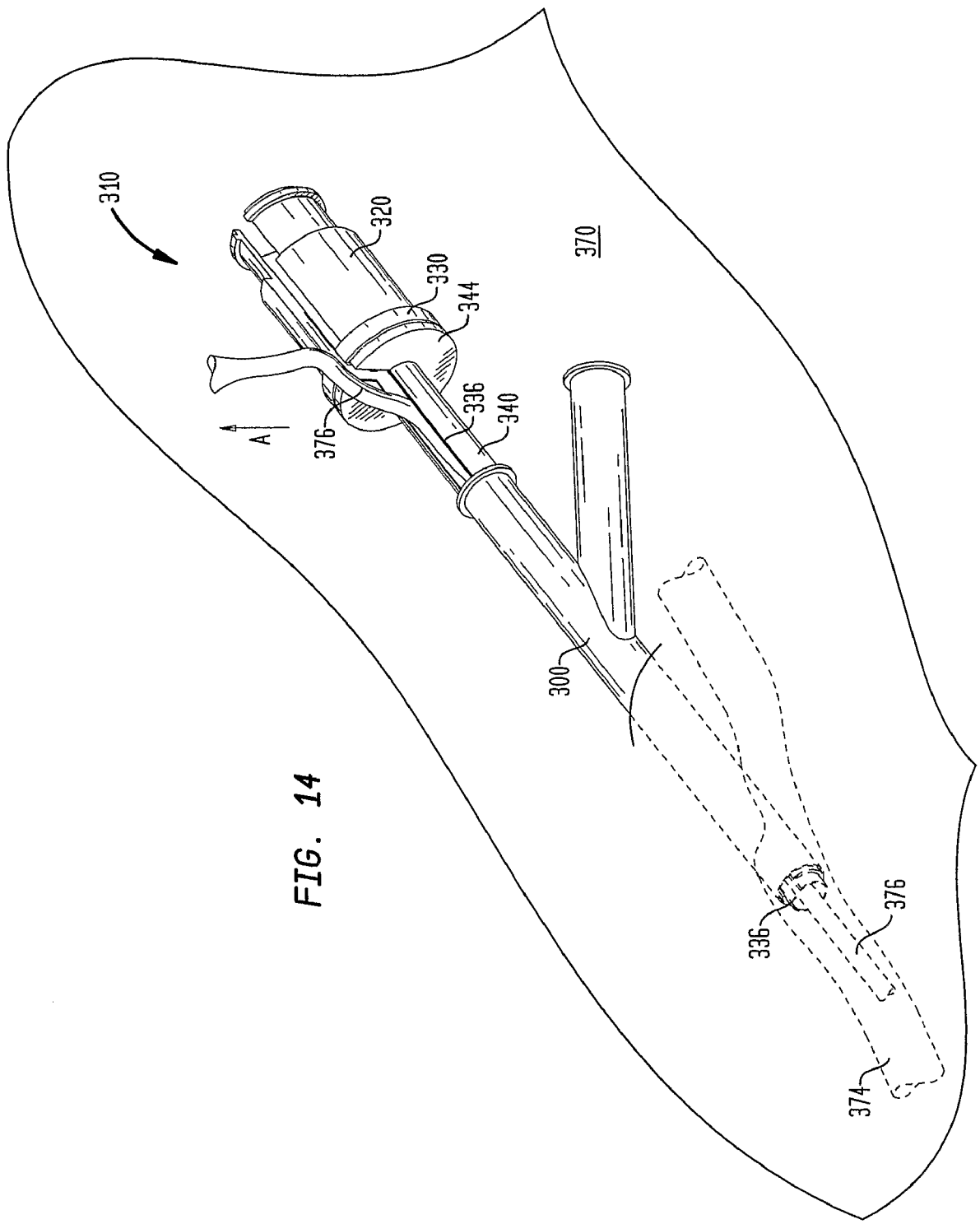
FIG. 14 shows the guide wire being lifted out of the slot of the wire introducer assembly shown in FIG. 13.

FIG. 13 shows wire introducer assembly 310 inserted into blood vessel 374 wherein wire introducer assembly 310 is in a second position wherein outer cylindrical tube 340 is rotated to align outer tube slot 342 and inner tube slot 336 to expose inner tube slot 336. As shown in FIG. 14, guide wire 376 can then be lifted out of wire introducer assembly 310 in the direction of Arrow A through inner tube slot 336. In the same manner described with respect to the embodiment shown in FIG. 9, wire introducer assembly 310 can then be removed from catheter assembly 300, leaving guide wire 376 in blood vessel 374. Because the inner cylindrical tube end 339 is blunt and is not used to pierce the patient's body in the wire introducer assembly, there is no need for a biasing mechanism to move the outer cylindrical tube longitudinally to cover the inner cylindrical tube end.

The vascular access needle assembly of the present invention can also be used as a biopsy needle assembly to remove body tissue to perform a biopsy. In this embodiment, as shown in FIGS. 15A-15D, a biopsy needle assembly 410 includes a housing 420 having an exterior surface 422. Housing 420 is generally cylindrical and defines a lumen. A shoulder 430 extends from exterior surface 422. A needle 434 is interconnected with housing 420. Needle 434 has a point 438 and a slot 436 along its length. A sheath 440 has a slot 442 extending along its length. The edges of one or both of sheath slot 442 and needle slot 436 are sharp to facilitate tissue cutting for biopsy samples. Sheath 440 can be interconnected to a sheath housing 444 which can be located between the ends of sheath 440. Sheath 440 rotatably and slidably engages needle 434 and substantially covers the length thereof.

Biopsy needle assembly 410 can also include a biasing mechanism for orienting sheath 440 and needle 434. A spring 480, or any other suitable biasing mechanism, can be positioned about sheath 440. Spring 480 is positioned between and bears against shoulder 430 and sheath housing 444. Biopsy needle assembly 410 can further include a rotational guide for orienting sheath 440 and needle 434. As shown the FIG. 15A, the rotational guide includes a rotational guide slot 490 on sheath 440. Rotational guide slot 490 has an upper horizontal portion 490A, a vertical portion 490B, and a lower horizontal portion 490C which extend along a portion of sheath 440. A rotational guide pin 495 extends from needle shaft 434 and is received in and is slidable along rotational guide slot 490.

Referring to FIG. 15A, biopsy needle assembly 410 is shown in a first position. Needle point 438 is exposed and sheath slot 442 is aligned with needle slot 436, exposing needle slot 436. In this first position, spring 480 is in a compressed position. Rotational guide pin 495 is positioned at a first end of upper horizontal guide slot portion 490A. In this position, biopsy needle assembly 410 is inserted into a tissue of a subject. With needle point 438 exposed and needle slot 436 exposed, the needle can pierce and access the tissue. As the biopsy needle assembly is introduced into the tissue, a sample of the tissue is forced into the core of needle 434.

As shown in FIG. 15B, in a second position, sheath 440 is rotated about needle 434 and covers needle slot 436. This motion forces the tissue against the sharp edges of either or both needle slot 436 and sheath slot 442 to cut the tissue and retain a tissue sample in the core of the needle. In this second position, spring 480 remains in a compressed position. Rotational guide pin 495 is positioned at a second end of upper horizontal guide slot portion 490A. The tissue sample can then be detached from the body tissue, for example, by attaching a syringe or like object to an open end of housing 422 to aspirate or apply negative suction to loosen or tear the tissue at needle tip 438.

In FIG. 15C, biopsy needle assembly 410 is shown in a third position, wherein sheath 440 slides longitudinally along needle 434 to cover needle point 438. Rotational guide pin 495 is positioned in vertical guide slot portion 490B allowing spring 480 to urge and slide sheath housing 444 along needle 434 such that sheath 440 covers needle point 438. Biopsy needle assembly 410 can then be removed from the insertion point.

In FIG. 15D, biopsy needle assembly 410 is shown in a fourth position, wherein sheath 440 is rotated about needle 434 to expose needle slot 436, while still covering needle point 438. Rotational guide pin 495 is positioned in lower horizontal guide slot portion 490C while spring 480 maintains sheath housing 444 positioned along needle 434 such that sheath 440 covers needle point 438. In this position of biopsy needle assembly 410, the tissue sample 499 in the needle core is exposed and can be removed.

Having thus described the invention in detail, it is to be understood that the foregoing description is not intended to limit the spirit and scope thereof. What is desired to be protected by Letters Patent is set forth in the appended claims.

What is claimed is:

1. A vascular access needle assembly comprising:
    a housing having a slot along its length;
    a needle interconnected with the housing, the needle having a point and a slot along its length, wherein the slots of the needle and housing are aligned to form a slot extending along the entire vascular access needle assembly;
    a sheath slidably and rotatably interconnected with and extending partially about the needle, the sheath having a slot;
    a lock mechanism for retaining the sheath in a first position and about the needle, exposing the needle point and covering the needle slot;
    a means for moving the sheath into a second position about the needle, covering the needle point and aligning the sheath slot and needle slot; and
    wherein said vascular access needle assembly further comprises a tether that is arranged to interconnect said housing and said sheath, and said means for moving said sheath into a second position includes a biasing mechanism.

2. The vascular access needle assembly according to claim 1, wherein the sheath slot and the needle slot are coextensive in width.

3. A method for inserting a guide wire into a blood vessel comprising the steps of:
    (a) inserting a vascular access needle assembly into a blood vessel;
    (b) inserting a guide wire through the vascular access needle assembly into the blood vessel;
    (c) moving a sheath on the vascular access needle assembly to cover a needle point and to expose a slot extending along the length of the vascular access needle assembly;
    (d) lifting the guide wire through the slot and out of the vascular access needle assembly; and
    (e) removing the vascular access needle assembly from the blood vessel so that the guide wire remains in the blood vessel.

4. The method according to claim 3, wherein the guide wire inserted in step (b) is adapted for micropuncture procedures by having a first diameter portion that is inserted into the blood vessel, and a second diameter portion that is larger than the first diameter portion and does not enter a housing of the vascular access needle assembly.

5. The method according to claim 4, further comprising the step of:
    (f) feeding the second diameter portion of the guide wire into the blood vessel.

6. The method according to claim 5, further comprising the step of:
    (g) inserting into the blood vessel a dilator arranged over the guide wire to perform a medical procedure.

7. A method for releasing a guide wire from a vascular insertion device comprising the steps of:
    (a) aligning the slots on an outer cylindrical sheath and an inner cylindrical member that form the insertion device by moving the outer cylindrical sheath to also cover the distal end of the inner cylindrical member;
    (b) lifting the guide wire through the slots and out of the vascular insertion device; and
    (c) removing the vascular insertion device from an insertion point leaving the guide wire inserted.

\* \* \* \* \*